(12) United States Patent
Takahashi et al.

(10) Patent No.: US 6,511,961 B1
(45) Date of Patent: Jan. 28, 2003

(54) CYCLIC PEPTIDES AND MEDICINAL USE THEREOF

(75) Inventors: Toshiya Takahashi, Kamakura (JP); Nobuo Saito, Yokohama (JP); Hideyuki Takeshige, Kamakura (JP); Toshiaki Tanaka, Zushi (JP); Mie Kainoh, Fujisawa (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 09/341,435

(22) PCT Filed: Nov. 12, 1998

(86) PCT No.: PCT/JP98/05096

§ 371 (c)(1), (2), (4) Date: Jul. 9, 1999

(87) PCT Pub. No.: WO99/25731

PCT Pub. Date: May 27, 1999

(30) Foreign Application Priority Data

Nov. 13, 1997 (JP) ............................................. 9-311692

(51) Int. Cl.$^7$ ........................ A61K 38/00; A61K 38/12; C07K 7/00
(52) U.S. Cl. ............................ 514/9; 530/317; 530/327; 530/328; 530/329; 514/14; 514/15; 514/16; 514/17
(58) Field of Search ................................ 514/9, 14, 15, 514/16, 17; 530/317, 329, 328, 327

(56) References Cited

U.S. PATENT DOCUMENTS

| | | | | |
|---|---|---|---|---|
| 6,001,809 A | * | 12/1999 | Thorsett | 514/15 |
| 6,087,330 A | * | 7/2000 | Kogan | 514/11 |

FOREIGN PATENT DOCUMENTS

| | | |
|---|---|---|
| WO | 92/00995 | 1/1992 |
| WO | 94/15958 | 7/1994 |
| WO | WO 96/00581 | 1/1996 |
| WO | 96/00581 | 1/1996 |
| WO | 96/01644 | 1/1996 |
| WO | WO 96/01644 | 1/1996 |
| WO | 96/40781 | 12/1996 |

OTHER PUBLICATIONS

Jackson et al J. Med. Chem. 1997, 40 3359–3368 Peptide Antagonist as Potential Anti–Inflammatory Agents.
Nowlin et al J. Biological Chem vol. 268, No. 27 9/25 pp. 20352–20359 A novel Cyclic Pentapeptide etc.
Wang et al Proc. Natl. Acad. Sci vol. 92, pp. 5714–5718 1995 The Crystal Structure of an N–terminal etc.
M.J. Elices et al., Clinical and Exper. Rheum. 11(suppl.8) S77–S80, 1993.
Ted A. Yednok et al., Nature 356(5), 63, 1992.
Kazuya Tsukamoto et al., Cellular Immuno., 165, 193, 1995.
Daniel K. Podolsky et al, J. Clin. Invest, 92, 372, 1993.
William M. Abraham et al., J. Clin. Invest. 93, 776, 1994.
Michael S. Mulligan et al., J. Clin. Invest, 91, 577, 1993.
Mitsuaki Isobe et al., J. Immuno., 153, 5810, 1994.
Andrew C. Issekuz et al., J. Exp. Med., 181, 1197, 1995; Barbadillo C. et al, Aethr. Rheum (suppl), 36, 95S(337), 1993.

* cited by examiner

Primary Examiner—Christopher S. F. Low
Assistant Examiner—Abdel A. Mohamed
(74) Attorney, Agent, or Firm—Nixon & Vanderhye P.C.

(57) ABSTRACT

Novel cyclic peptides having VLA-4 adhesion inhibiting activity, and their application as therapeutic agents for inflammatory disease, for example allergic inflammatory disease, or hepatitis. Cyclic peptides represented by formula (I)

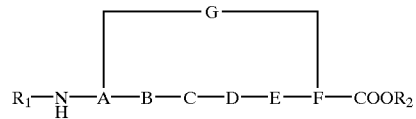

where A and F may be the same or different, and are both selected from L- or D-form Cys, homo-Cys, Pen and Mpr, or both from the group comprising Asp, Glu, Aad, Dpr, Dab and Orn, B is selected from L-or D-form Ala, Ala(t-Bu), Val, Leu, Ile, aIle, Abu, Nle, Nva, Tle, Cha, Chg, Phe, Phg, Trp, Ala(3-Bzt), Ala(1-Naph), Ala(2-Naph), Ala(2-Pyr), Ala(2-Qui), His, Thi, Ala(4-Thz), 2-Abz, Pro, homo-Pro and Tic, C is selected from L-form Asp analogues, Gle analogues, Aad analogues, Asn analogues, Gln analogues, Ser, Ser (OMe), homo-Ser, Dpr, Dab, Orn, Met, Met)O), Met($O_2$), aIle, Nle, Nva, Chg, Phg, Tyr and Tle, D is selected from L- or D-form Tyr, Ser, homo-Ser, Leu, Ile, AIle, Nle, Nva, Chg, Cha, Val, Ala(t-Bu), Abu, Tle, Ala, Phg, homo-Phe, Phe, Ala(2-Naph), Ala(2-Pyr), Ala(3-Bzt), Ala(1-Naph), Ala(2-Qui), Thi, Ala(4-Thz), 2-Abz, Trp and His, E is selected from L- or D-form Leu, Ile, aIle, Nle, Nva, Chg, Cha, Tle, Phg, homo-Phe, Ala(2-Naph), Ala(2-Pyr), Ala(3-Bzt), Ala(1-Naph), Ala(2-Qui), Thi, Ala(4-Thz), 2-Abz and His, G represents a disulphide bond or amide bond, $R_1$ represents hydrogen or an acyl group, and $R_2$ is hydrogen or an alkyl group, or salts thereof, and to their use in treating inflammatory diseases.

6 Claims, 2 Drawing Sheets

Figures in brackets ( ) indicates the percentage suppression

CYCLIC PEPTIDES AND MEDICINAL USE THEREOF

TECHNICAL FIELD

The present invention relates to novel cyclic peptides and salts thereof which have a VLA-4 adhesion molecule inhibition action useful as a therapeutic agent for inflammatory diseases, for example allergic inflammatory diseases such as bronchial asthma, atopic dermatitis and allergic rhinitis, hepatitis, nephritis, chronic rheumatoid arthritis, autoimmune disease, rejection reactions following organ transplantation, type I diabetes, Crohn's disease, or postoperative restenosisis prevention and arteriosclerosis, and to medicinal uses thereof.

BACKGROUND ART

VLA-4 (very late antigen-4) is an adhesion molecule which is expressed on white blood cells such as lymphocytes, monocytes, basophils and eosinophils, and it belongs to the VLA family. VLA-4 has a heterodimer structure comprising an α chain and β chain, and is also referred to as $α_4β_1$, or CD49d/CD29. It plays a part in cell-cell and cell-extracellular matrix interactions, and is involved in the infiltration of white blood cells into sites of inflammation. VCAM-1 (vascular cell adhesion molecule-1) which is present on vascular endothelial cells and fibronectin of the extracellular matrix is known as an adhesion molecules which interact with VLA-4.

The binding site for VLA-4 on fibronectin is a fibronectin fragment referred to as CS-1 and, within this fragment, the smallest unit of amino acids necessary for binding is reported to be the three amino acid residues leucine-aspartic acid-valine. Furthermore, chain form or cyclic peptide VLA-4 adhesion inhibiting compounds based on the three amino acid residues leucine-aspartic acid-valine have been reported (WO95/15973).

On the other hand, with regard to VCAM-1, which is the other adhesion molecule which interacts with VLA-4, it is known that its manifestation mainly on vascular endothelial cells is increased by stimulation by cytokines such as IL-1, TNF-α and IL-4, and that it interacts with the VLA-4 present on cells such as lymphocytes, NK cells, monocytes andfeosinophils. VLA-4 and VCAM-1 play a part in the process:of white blood cell infiltration into inflammation sites from blood vessels and, from this point of view, the interaction between VLA-4 and VCAM-1 in the inflammatory response is extremely important.

Of the adhesion molecules, VCAM-1 belongs to an immunoglobulin super family, and 7-Ig-like-domain VCAM-1 and 6-Ig-like-domain VCAM-1 are known. Binding sites for VLA-4 on VCAM-1 are present at domain 1 and domain 4 and it has been made clear from the results of VCAM-1 mutation that, in particular within these domains, glutamine-isoleucine-aspartic acid-serine-proline, which is the amino acid sequence on the CD loop, is important in the binding with VLA-4 (J. Cell Bio., 125, 1395 (1994), J. Cell Bio., 124, 601 (1994), J. Cell Bio., 125, 215 (1994) and J. Cell. Science, 107, 2127 (1994)). Furthermore, taking glutamine-isoleucine-aspartic acid-serine-proline as the basic peptide, J. H. Wang et al have reported the cyclic peptide Cys* Gln Ile Asp Ser Pro Cys* SEQ ID NO:58 (where Cys*Cys* indicates a disulphide bond) which has a VLA-4 adhesion inhibiting activity (Proc. Natl. Acad. Sci. USA, 92, 5714 (1995)). Again, inhibitors which were designed making reference to the anti-VLAα$_4$ antibody CDR3 amino acid sequence and the VCAM-1 EF loop amino acid sequence.

It has been made clear from animal models, specifically contact hypersensitivity and delayed hypersensitivity models (mouse and rat), experimental autoimmune encephalomyelitis models (mouse and rat), nephrotic nephritis models (rat), passive cutaneous anaphylaxis models (guinea pig), immune complex-induced lung injury models (rat), spontaneous colitis models (monkey) and asthma models (sheep), where anti-VLA-4 antibodies have been used, that VLA-4 plays an important role in the inflammatory response.

Conventional drugs which are used against inflammatory diseases such as allergic inflammation and chronic rheumatoid arthritis possess the action of inhibiting the action of chemical transmitters, or the action of suppressing the production of chemical transmitters or the action of inhibiting the production of active oxygen, etc, but since they do not have, as their main action, the action of suppressing the process of white blood cell infiltration to the inflammation site, they cannot suppress the progress of inflammation. As stated earlier, the adhesion molecules VLA-4 and VCAM-1 contribute mainly to the process of white blood cell infiltration to the inflammation site and so novel cyclic peptides which have the activity of inhibiting the adhesion of VLA-4 and VCAM-1 may be expected to suppress white blood cell infiltration and may be considered to have considerable potential as therapeutic agents effective against the aforesaid diseases. Hitherto, there have been reported inhibiting compounds synthesized with reference to CS-1, which is the binding site for VLA-4 on the fibronectin side, and the anti-VLAα$_4$ antibody epitope, but except for Wang et al, there have been no reports of novel peptide compounds created with reference to the binding site on the VCAM-1 side, and to the medicinal applications thereof.

DISCLOSURE OF INVENTION

The objective of the present invention lies in creating compounds with reference to the binding site on the VCAM-1 side, and offering novel peptides.

As a result of painstaking investigations with reference to the binding site on the VCAM-1 side, the present inventors discovered that, by creating novel cyclic peptides with a marked VCA-4 adhesion inhibition activity, these cyclic peptides can be used as therapeutic agents for, amongst inflammatory diseases, allergic inflammatory diseases and hepatitis, and the a present invention has been perfected based on this discovery.

Specifically, the present invention, has the following constitution.

It relates to cyclic peptides represented by formula (I)

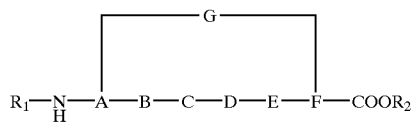

[where, in formula (I),
A and F may be the same or different, and are both selected from the group comprising; L- or D-form Cys, homo-Cys, Pen and Mpr, or both from the group comprising Asp, Glu, Aad, Dpr, Dab and Orn,
B is selected from the group comprising L- or D-form Ala, Ala(t-Bu), Val, Leu, Ile, aIle, Abu, Nle, Nva, Tle, Cha, Chg, Phe, Phg, Trp, Ala(3-Bzt), Ala(1-Naph), Ala(2-

Naph), Ala(2-Pyr), Ala(2-Qui), His, Thi, Ala(4-Thz), 2-Abz, Pro, homo-Pro and Tic, C is selected from the group comprising L-form Asp analogues, Glu analogues, Aad analogues, Asn analogues, Gln analogues, Ser, Ser(OMe), homo-Ser, Dpr, Dab, Orn, Met, Met(O), Met(O$_2$), aIle, Nle, Nva, Chg, Phg, Tyr and Tle and, when C is selected from L-form Asp analogues, Glu analogues and Aad analogues, then it is of formula (II)

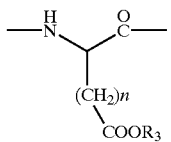

n=1 Asp n=2 Glu n=3 Aad
(where R$_3$ may be hydrogen or an alkyl group and, when R$_3$ is an alkyl group, it comprises a C$_1$ to C$_6$ straight chain or branched alkyl group) and, when C is selected from.Asn analogues and Gln analogues, then it is of formula (III)

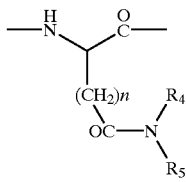

n=1 Asn n=2 Gln
(where R$_4$ and R$_5$ may be the same or different, and may respectively be hydrogen or an alkyl group and, in the case where R$_4$ or R$_5$ is an alkyl group, it comprises a C$_1$ to C$_6$ straight chain or branched alkyl group), D is selected from the group comprising L- or D-form Tyr, Ser, homo-Ser, Leu, Ile, aIle, Nle, Nva, Chg, Cha, Val, Ala(t-Bu), Abu, Tle, Ala, Phg, homo-Phe, Phe, Ala(2-Naph), Ala(2-Pyr), Ala(3-Bzt), Ala(1-Naph), Ala(2-Qui), Thi, Ala(4-Thz), 2-Abz, Trp and His, E is selected from the group comprising L- or D-form Leu, Ile, aIle, Nle, Nva, Chg, Cha, Tle, Phg, homo-Phe, Ala(2-Naph), Ala(2-Pyr), Ala(3-Bzt), Ala(1-Naph), Ala(2-Qui), Thi, Ala(4-Thz), 2-Abz and His, G represents a, disulphide bond or amide bond, R$_1$ may be hydrogen or an acyl group, and in the case where R$_1$ is an acyl group, then it is. of formula (IV)

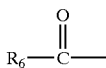

(where R$_6$ comprises a C$_1$ to C$_6$ straight chain or branched alkyl group, a C$_4$ to C$_8$ cycloalkyl group, a C$_5$ to C$_{11}$ alkylcycloalkyl group, a C$_6$ to C$_{14}$ aryl group or a C$_7$ to C$_{11}$ aralkyl group), and R$_2$ may be hydrogen or an alkyl group and, in the case where R$_2$ is an alkyl group, it is a C$_1$ to C$_6$ straight chain or branched alkyl group], or the salts thereof, and to medicinal applications thereof.

BEST MODE FOR CARRYING OUT THE INVENTION

Figure 1:
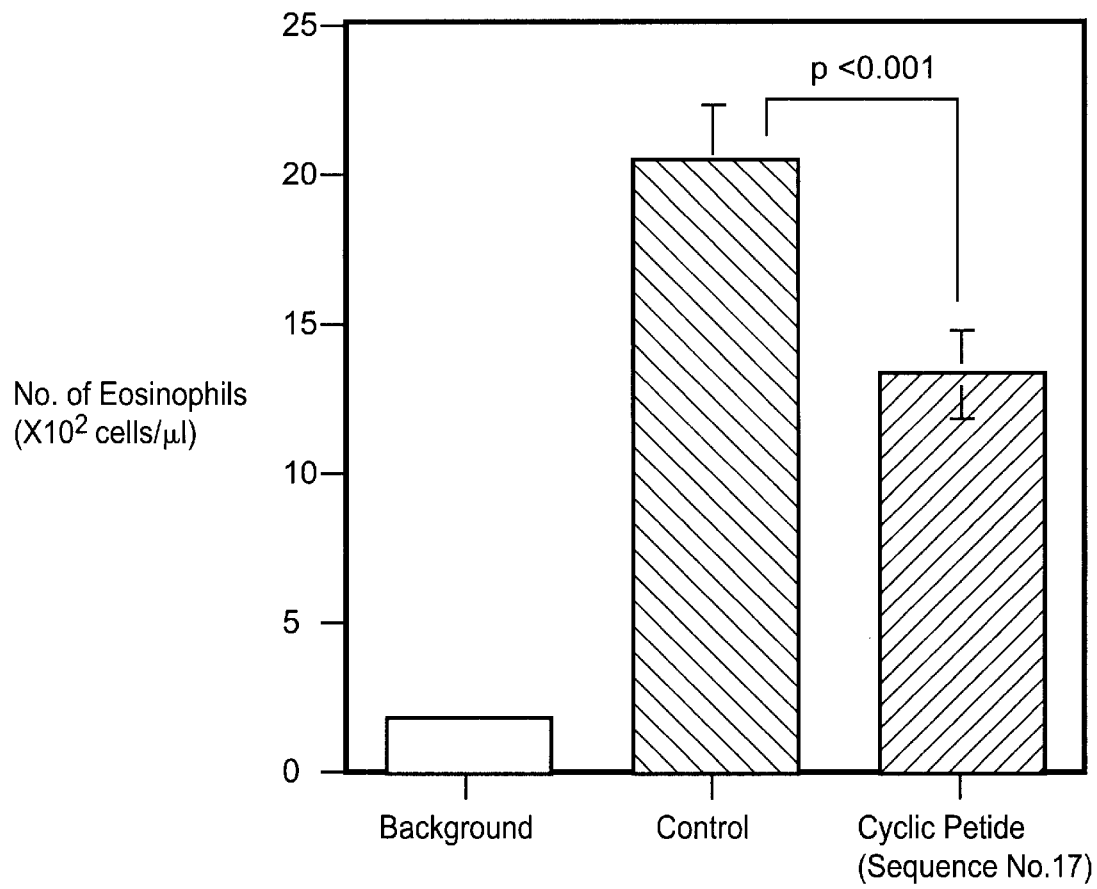
FIG. 1 shows the fact that, in the mouse peritonitis model, cyclic peptide shown in SEQ ID NO:17 significantly suppressed eosinophil accumulation in the abdominal cavity caused by antigen challenge.

That is to say, the present invention relates to cyclic peptides represented by formula (I)

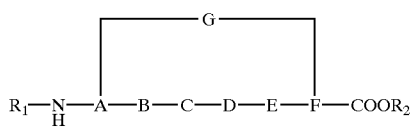

where, in formula (I),

A and F may be the same or different, and are both selected from the group comprising L- or D-form Cys, homo-Cys, Pen and Mpr, or both from the group comprising Asp, Glu, Aad, Dpr, Dab and Orn, B is selected from the group comprising L- or D-form Ala, Ala(t-Bu), Val, Leu, Ile, aIle, Abu, Nle, Nva, Tle, Cha, Chg, Phe, Phg, Trp, Ala(3-Bzt), Ala(1-Naph), Ala(2-Naph), Ala(2-Pyr), Ala(2-Qui), His, Thi, Ala(4-Thz), 2-Abz, Pro, homo-Pro and Tic, C is selected from the group comprising L-form Asp analogues, Glu analogues, Aad analogues, Asn analogues, Gln analogues, Ser, Ser(OMe), homo-Ser, Dpr, Dab, Orn, Met, Met(O), Met(O$_2$), aIle, Nle, Nva, Chg, Phg, Tyr and Tle and, when C is selected from the L-form Asp analogues, Glu analogues and Aad analogues, then it is of formula (II)

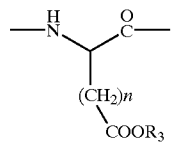

n=1 Asp n=2 Glu n=3 Aad
where R$_3$ may be hydrogen or an alkyl group and, when R$_3$ is an alkyl group, it is a methyl group, ethyl group, n-propyl group, isopropyl group, n-butyl group, isobutyl group, 2-methyl-propyl group, n-pentyl group, 1-methyl-butyl group, 2-methyl-butyl group, 3-methyl-butyl group, 1,1-dimethyl-propyl group, 2,2-dimethyl-propyl group, 1,2-dimethyl-propyl group, n-hexyl group, 1-methyl-pentyl group, 2-methyl-pentyl group, 3-methyl-pentyl group, 4-methyl-pentyl group, 1,1-dimethyl-butyl group, 2,2-dimethyl-butyl group, 3,3-dimethyl-butyl group, 1,2-dimethyl-butyl group, 1,3-dimethyl-butyl group, 2,3-dimethyl-butyl group, 1,1-dimethyl-2-methyl-propyl group, 1-methyl-2,2-dimethyl-propyl group or the like, and when C is selected from Asn analogues and Gln analogues, then it is of formula (III)

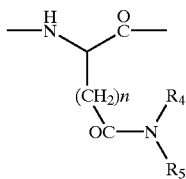

n=1 Asn  n=2 Gln where $R_4$ and $R_5$ may be the same or different, and may respectively be hydrogen or an alkyl group and, in the case where $R_4$ or $R_5$ is an alkyl group, it is a methyl group, ethyl group, n-propyl group, n-butyl group, n-pentyl group, n-hexyl group or the like, D is selected from the group comprising L- or D-form Tyr, Ser, homo-Ser, Leu, Ile, aIle, Nle, Nva, Chg, Cha, Val, Ala(t-Bu), Abu, Tle, Ala, Phg, homo-Phe, Phe, Ala(2-Naph), Ala(2-Pyr), Ala(3-Bzt), Ala(1-Naph), Ala(2-Qui), Thi, Ala(4-Thz), 2-Abz, Trp and His, E is selected from the group comprising L- or D-form Leu, Ile, aIle, Nle, Nva, Chg, Cha, Tle, Phg, homo-Phe, Ala(2-Naph), Ala(2-pyr), Ala(3-Bzt), Ala(1-Naph), Ala(2-Qui), Thi, Ala(4-Thz), 2-Abz and His, G represents a disulphide bond or amide bond, $R_1$ may be hydrogen or an acyl group and, in the case where $R_1$ is an acyl group, it is of formula (IV)

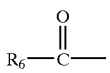

where $R_6$ is a methyl group, ethyl group, n-propyl group, isopropyl group, n-butyl group, isobutyl group, 2-methyl-propyl group, n-pentyl group, 1-methyl-butyl group, 2-methyl-butyl group, 3-methyl-butyl group, 1,1-dimethyl-propyl group, 2,2-dimethyl-propyl group, 1,2-dimethyl-propyl group, n-hexyl group, 1-methyl-pentyl group, 2-methyl-pentyl group, 3-methyl-pentyl group, 4-methyl-pentyl group, 1,1-dimethyl-butyl group, 2,2-dimethyl-butyl group, 3,3-dimethyl-butyl group, 1,2-dimethyl-butyl group, 1,3-dimethyl-butyl group, 2,3-dimethyl-butyl group, 1,1-dimethyl-2-methyl-propyl group, 1-methyl-2,2-dimethyl-propyl group, cyclohexyl group, cyclohexylmethyl group, cyclohexylethyl group, cyclopentyl group, cyclopentylmethyl group, cyclopentylethyl group, phenyl group, o-, m- or p-tolyl group, naphthyl group, anthranyl group, phenylmethyl group, phenylethyl group, phenylpropyl group, or the like, and $R_2$ may be hydrogen or an alkyl group and, in the case where $R_2$ is an alkyl group, it is a methyl group, ethyl group, n-propyl group, isopropyl group, n-butyl group, isobutyl group, 2-methyl-propyl group, n-pentyl group, 1-methyl-butyl group, 2-methyl-butyl group, 3-methyl-butyl group, 1,1-dimethyl-propyl group, 2,2-dimethyl-propyl group, 1,2-dimethyl-propyl group, n-hexyl group, 1-methyl-pentyl group, 2-methyl-pentyl group, 3-methyl-pentyl group, 4-methyl-pentyl group, 1,1-dimethyl-butyl group, 2,2-dimethyl-butyl group, 3,3-dimethyl-butyl group, 1,2-dimethyl-butyl group, 1,3-dimethyl-butyl group, 2,3-dimethyl-butyl group, 1,1-dimethyl-2-methyl-propyl group, 1-methyl-2,2-dimethyl-propyl group, or the like, but, preferably, cyclic hexapeptides where C is selected from the group comprising L-form Ser, Ser(OMe), homo-Ser, Dpr, Dab, Orn, Met(O), Met($O_2$), aIle, Nle, Nva, Chg, Phg, Tyr and Tle, and D is selected from the group comprising L- or D-form Tyr, Ser, homo-Ser, Leu, Ile, aIle, Nle, Nva, Chg, Val, Ala(t-Bu), Abu, Tle, Ala, Phg, homo-Phe, Ala(2-Naph), Ala(2-Pyr), Ala(3-Bzt), Ala(1-Naph), Ala(2-Qui), Thi, Ala(4-Thz), 2-Abz, Trp and His, and to drugs which are characterized in that they contain a cyclic hexapeptide represented by formula (I), or pharmacologically permitted salt thereof, as an effective component.

The VCAM-1 binding site for VLA-4 is glutamine-isoleucine-aspartic acid-serine-proline, and it is presumed that the aspartic acid in particular is important for the manifestation of activity. The cyclic peptides of the present invention manifest satisfactory activity even where no aspartic acid is present in the sequence. Furthermore, the cyclic peptides of the present invention are stable in mouse serum. For example, the cyclic peptide of Sequence No. 17 is stable for 24 hours in mouse serum.

In formula (I), the amino acids in the span A—B—C—D—E—F are bonded by amide bonds while, between A—F through G, bonding is by an amide bond or disulphide bond, and ring formation is shown.

As the salts of the cyclic peptides oft formula (I) of the present invention, there are inorganic acid addition salts (for example the hydrochloride, sulphate, phosphate and the like) and the salts of organic acids (for example the acetate, trifluoroacetate, propionate, citrate, oxalate, succinate, tartrate, malate and the like).

The cyclic peptides of formula (I) of the present invention can be synthesized by both solid phase synthesis methods and liquid phase synthesis methods. In synthesizing the compounds of the present invention, the chain form peptide which constitutes the raw material for the cyclic peptide was synthesized by a method of solid phase synthesis (Fmoc method, Shimadzu Corporation, Automatic Peptide Syntheziser PSSM-8). As the resin, there was used Fmoc-protected amino acid bonded resin, or Fmoc-protected resin. DMF was employed as the solvent, PyBOP-HOBT was used as the coupling agent and synthesis was performed following the usual procedure.

Specifically, peptide synthesis on the resin was conducted by repeated cycles of washing the resin with DMF, Fmoc group deprotection with 30% piperidine-DMF solution, coupling with amino acid, removal from the reaction system of excess amino acid and coupling reagent, and washing with DMF. After the completion of peptide synthesis using the synthesizer, the resin was washed with methanol and then t-butyl methyl ether, and dried using a vacuum pump. Next, the synthesized peptide was separated from the resin. As reagents, generally TFA, anisole and EDT were used but, where tryptophan was present in the peptide, reaction was carried out with the addition of 2-methylindole to the aforesaid reagents. Subsequently, ether was added to the peptide solution and a precipitate produced, which was separated. by centrifuging. The supernatant was discarded, and washing carried out by the addition of ether to the residue, followed by centrifugal separation. The supernatant was discarded and drying performed using a flow of nitrogen and the crude peptide obtained. The crude peptide was purified using HPLC (solvent: 0.1% TFA-water and 0.1% TFA-acetonitrile mixed solvent), after which freeze drying was carried out.

Next, the chain-form peptide was converted to the cyclic peptide. There are various possible methods for converting a chain-form peptide to a cyclic peptide by disulphide bond formation. Examples include the method using iodine, the method using NIS (N-iodosuccinimide), the method thallium trifluoroacetate, the method using potassium ferrocyanide, the air oxidation method, the method using trimethylsilylchloride-diphenylsulphoxide, and the method using DMSO (dimethylsulphoxide)-hydrochloric acid. In particular, the method using potassium ferrocyanide and the method using DMSO (dimethylsulphoxide)-hydrochloric acid are preferred for the peptide cyclization conditions in the present invention, but there is no restriction thereto. When potassium ferrocyanide is used as the cyclization reagent, the chain-form peptide and 0.1 M potassium ferrocyanide are dissolved in distilled water (peptides which are insoluble or sparingly soluble in water are preferably dissolved in a small amount of DMSO after which the distilled water is added). and, using a pH meter, the pH of the respective solutions adjusted to 6–9. The pH is preferably 7–8, but there is no restriction thereto. The aqueous solution of the peptide is added dropwise to the aforesaid adjusted aqueous solution of potassium ferrocyanide at 0.01 ml/min to 0.8 ml/min. Dropwise addition at 0.05 ml/min to 0.4 ml/min is preferred but there is no restriction thereto. The preferred pH state of the reaction solution is 7–8, and where it shifts either to the acidic or alkaline side it is desirable that the pH adjustment be carried out with the addition of dilute aqueous ammonia or dilute hydrochloric acid. From 1 to 10 equivalents of the potassium ferrocyanide is used in terms of the peptide, but a sufficient reaction rate is obtained even with 1–2 equivalents. Following completion of the dropwise addition of the aqueous solution, the disappearance of the chain-form peptide is confirmed by analytical HPLC after which purification is performed by preparative HPLC and freeze drying carried out.

Where there is employed thee method using dimethylsulphoxide-hydrochloric acid as the cyclization method, synthesis can be carried out in accordance with the method of Fujii et al. Specifically, the chain-form peptide in which Acm (acetamidomethyl) has been employed as the thiol-protecting group is dissolved in TFA and, in the presence of anisole, 10 equivalents of silver trifluoroacetate is introduced and stirring carried out at room temperature. Ether is added to the reaction solution and centrifugal separation performed, after which the ether layer is discarded, then ether again added to wash the residue, following which centrifugal separation is performed and the ether layer discarded.

The residue is dried using a nitrogen flow, after which 50% DMSO-1N HCl is added to the residue, then stirring carried out overnight and the precipitate filtered off. After the filtrate has been diluted with distilled water, purification is performed by HPLC (solvent: 0.1% TFA-water and 0.1% TFA-acetonitrile mixed solvent) and freeze drying carried out.

The methods for converting a chain-form peptide to a cyclic peptide by amide bonding can be carried out on peptide which has been detached from the resin or peptide bonded to the resin, and the conversion can be performed by the same kinds of methods as are used for coupling together amino acids. Specifically, there are the active ester method, the mixed acid anhydride method, the azide method, the acid chloride method, and methods using coupling agents (DPPA (diphenylphosphoryl azide), DCC (N,N'-dicyclohexylcarbodiimide), EDCI (N-ethyl-N'-3-dimethylaminopropylcarbodiimide), CDI (carbonyldiimidazole), BOP-Cl (bis(2-oxo-3-oxazolidinyl)phosphinic chloride and PyBOP (benzotriazol-1-yl-oxy-tris-pyrrolidino-phosphonium-hexafluorophosphate)), etc, but there is no restriction to these particular methods.

In cases where PyBOP was used as the coupling agent, DMF was added as the solvent, then the PyBOP, HOBt and NMM added, and stirring carried out at room temperature, to effect conversion to the cyclic peptide.

As the method for investigating the adhesion inhibiting activity in terms of VLA-4, there can be used an adhesion measuring system for cells such as Ramos cells and Jurkat cells, and fibronectin or a fibronectin fragment, for example a peptide consisting of the CS-1 sequence (Gly Pro Glu Ile Leu Asp Val Pro Ser Thr SEQ ID NO:59) [hereinafter referred to as the CS-1 peptide], immobilized on an immunoplate. Furthermore, as another method, there can be used a binding measurement system for VLA-4 protein and fibronectin or a fibronectin fragment, for example the CS-1 peptide, immobilized on an immunoplate or the like. In the present invention, it is preferred that the inhibiting activity of a compound be evaluated in a binding measurement system for a VLA-4 and immunoglobulin chimeric protein (VLA-4-IgG chimeric protein) and a peptide containing the CS-1 sequence (WO98/032771), but there is no restriction thereto. Reference here to VLA-4-IgG chimeric protein means a heterodimer complex molecule formed when a VLA-4 $\alpha_4$ and immunoglobulin chimeric protein (referred to hereinafter as the VLA$\alpha_4$.IgG chimeric protein) and a VLA-4 $\beta_1$ and immunoglobulin chimeric protein (referred to hereinafter as the VLA$\beta_1$.IgG chimeric protein) undergo association. Moreover, for the immunoglobulin, there can be used heavy or light chains of IgG, IgM or the like, and in the present invention IgG1 heavy chains were used. When observing the cyclic peptide inhibition effect, it is best to use a previously prepared mixture of the $\alpha_4$.IgG heavy chain-$\beta_1$.IgG heavy chain chimeric protein heterodimer complex and the test material.

In this Specification, when the amino acids and peptides, etc, are expressed in abbreviated form, these conform to abbreviations based on the IUPAC-IUB Joint Commission on Biochemical Nomenclature or are the abbreviations generally used in the field. Some examples are provided.

Gly or G: glycine, Ala or A: alanine, Ala(t-Bu): t-butylalanine, Val or V: valine, Nva: Norvaline, Nle: norleucine, Ile or I: isoleucine, aIle: allo-isoleucine, Abu: 2-aminobutanaic acid, Tle: t-butylglycine, Lys or K: lysine, Orn: ornithine, Dpr: 2,3-diaminopropionic acid, Dab: 2,4-diaminobutanoic acid, His or H: histidine, Asp or D: aspartic acid, Asn or N: asparagine, Glu or E: glutamic acid, Gln or Q: glutamine, Aad: 2-aminoadipic acid, Cys or C: cysteine, homo-Cys: homocysteine, Pen: penicillamine, Mpr: 3-mercaptopropionic acid, Pro or P: proline, homo-Pro: homoproline, Trp or W: tryptophan, Phe or F: phenylalanine, Phg: phenylglycine, homo-Phe or Hph: homophenylalanine, Ala(1-Naph): 1-naphthylalanine, Ala(2-Naph): 2-naphthylalanine, Ala(2-Pyr): 2-pyridylalanine, Ala(3-Bzt): benzothienylalanine, Thi: thienylalanine, Ala(4-Thz): 4-thiazolylalanine, Ala(2-Qui): 2-quinoylalanine, Cha: cyclohexylalanine, Chg: cyclohexylglycine, Tic: 1,2,3,4-tetrahydroisoquinoline-3-carboxylic acid, 2-Abz: 2-aminobenzoic acid, Thr or T: threonine, Tyr or Y: tyrosine, Ser or S: serine, homo-Ser or Hse: homoserine, Ser(OMe) or S(OMe) serine methyl ether, Met or M: methionine, Met(O): methionine sulphoxide and Met($O_2$): methionine sulphone.

Furthermore, the reagents employed in this Specification are denoted by the following symbols.

Fmoc: 9-fluorenylmethoxycarbonyl, HOBt: N-hydroxybenzotriazole, PIP: piperidine, NMM: N-methylmorpholine, TFA: trifluoroacetic acid, EDT: 1,2-ethanedithiol, DPPA: diphenylphosphoryl azide, DCC: N,N'-dicyclohexylcarbodiimide, EDCI: N-ethyl-N'-3- dimethylaminopropylcarbodiimide, CDI: carbonyldiimidazo BOP-C-1: bis(2-oxo-3-oxazolidinyl)phosphonic chloride, PyBOP: benzotriazol-1-yl-oxy-tris-pyrrolidino-phosphonium-hexafluorophosphate, DMF: dimethylformamide The novel cyclic peptides of the present invention have a VLA-4 adhesion inhibiting action, and so can be used as a therapeutic agent for inflammatory diseases by suppressing the infiltration of white blood cells to an inflammation site. Here, inflammatory diseases refer to, for example, bronchial asthma, atopic dermatitis, allergic rhinitis and other such allergic inflammatory diseases, hepatitis, nephritis, chronic rheumatoid arthritis, multiple sclerosis and other such autoimmune diseases, rejection reactions following organ transplantation, type I diabetes, Crohn's disease and the like. In addition, they can be used. for postoperative restenosisis prevention and as therapeutic agents for arteriosclerosis.

In the present invention, the effects of the cyclic peptides obtained by the aforementioned methods are exemplified using mouse inflammation models, but there is no restriction thereto.

Various models have been reported as allergic inflammation models, and in the peritonitis model with Ascaris or ragweed pollen as the antigen, or in the ear edema model using dinitrofluorobenzene or oxazolone as the hapten antigen, the effects of the test compounds are investigated by measuring the suppression of the number of white blood cells accumulating in the abdominal cavity or the swelling of the ear, induced by the antigen. More preferably, as the antigen, Ascaris antigen is employed in the peritonitis model and dinitrofluorobenzene is used in the ear oedema model. Of the allergic inflammations in humans, these models reflect IgE-mast cell dependent type type-I allergic reaction and cell mediated immunity type type-IV allergic reaction, so are known to be effective as drug evaluation models ("Handbook of Experimental Immunology," vol. 2, Chapter 7, Miller, S. D. and Jenkins, M. K. (1986) Blackwell Scientific Publications, Oxford; Spicer, B. A et al., Int. Arches Allergy Appl. Immun., 81, 81–84 (1986)). In humans, as examples of diseases where the type I allergic reaction plays a part there are bronchial asthma, atopic dermatitis, allergic rhinitis and the like, while examples of disease where the type-IV allergic reaction plays a part are contact dermatitis, atopic dermatitis and the like.

Regarding hepatitis models, it is possible to confirm the effects of a test compound using a ConA-induced hepatitis model and employ the suppression effect on the rise in ALT and AST in the serum as an index. Of human hepatitis forms, this model can be regarded as resembling the T-cell mediated liver injury mechanism (Lohse, A. W. et al, p191–199 in "Autoimmune disease models" ed. Cohen, I. R. and Miller, A. (1994) Academic Press, California; Tiegs, G. et al, J. Clin. Invest. 90, 196–203 (1992); Mizushima, H. et al, J. Exp. Med. 179, 1529–1537 (1994)). As examples of T-cell mediated liver injury, there are acute viral hepatitis, chronic viral hepatitis, drug-induced liver injury, fulminant hepatitis, autoimmune liver injury, chronic hepatitis and the like.

When a cyclic peptide of the present:invention is used as an aforesaid therapeutic agent, it may be employed as it is or there may be included pharmacologically permitted carriers (supports, fillers, diluents) to produce a composition. Again, as dosage forms there can be used powders, granules, tablets, capsules, injections, suppositories, ointments, slow-release agents and the like. As administration routes for a cyclic peptide of the present invention, there may be considered oral, or nasal, pulmonary, subcutaneous, intramuscular, intravenous, intra-arterial or other parenteral routes. The cyclic peptides of the present invention are stable materials, so can be kept-as a solution in physiological saline, but can also have the form of a frozen ampoule with the addition of mannitol or sorbitol, and be dissolved at the time of use. The cyclic peptides of the present invention can be administered in the free form or, as a salt with a base or an acid-addition salt.

The dose will vary with the disease, symptoms, subject and administration method, etc, but in the case of administration by injection to an adult patient, and taking the cyclic peptide free form, base salt and acid added salt together as the free form, it is preferred that there generally be used about 0.1 mg to 1000 mg/kg as a single dose. While it will differ depending on the cyclic peptide administered and the particular patient, it is more preferred that about 50 mg–100 mg/kg be administered three times per day.

EXAMPLES

Below, the invention will be explained in more specific terms by providing examples. Now, of the amino acids described in the examples, where an amino acid is not particularly described as having the D-form, the L-form is indicated.

Example 1

Synthesis of Cyclic Peptide by the Potassium Ferrocyanide Method/Synthesis of C*IDYLC* (SEQ ID NO:3)

0.18 ml of 0.1 N potassium ferrocyanide was added to 9 ml of distilled water and, using 1% aqueous ammonia solution, the pH was adjusted to 7.5–8.0. 6.6 mg of CIDYLC.CF$_3$COOH was dissolved in 9 ml of distilled water and, using 1% aqueous ammonia solution, the pH was adjusted to 7.5–8.0. The solution of dissolved CIDYLC.CF$_3$COOH was then added dropwise at a rate of 0.2 ml/min to the aqueous potassium ferrocyanide solution. At this time, the pH of the reaction solution was maintained at 7.5–8.0 by the addition as required of 1% ammonia. The reaction solution was filtered with a membrane filter (0.45 mm) and the filtrate purified by high performance liquid chromatography (column: YMC-Pack R&D ODS Size: 250×20 mm I.D. Particle: S-5 mm, 120A, 0.1% TFA-distilled water-0.1% TFA-acetonitrile gradient), after which, when the eluate was freeze dried, 4.0 mg (5.5 mmol) of C*IDYLC*CF$_3$COOH was obtained (yield 61%).

Example 2

Synthesis of Cyclic Peptide by the DMSO-HCl Method/Synthesis of C*IDHLC* (SEQ ID NO:4)

68 ml (0.63 mmol) of anisole and 79 mg (0.31 mmol) of silver trifluoromethanesulphonate were added to a trifluoroacetic acid solution (5 ml) of 30 mg (31 mmol) of C(Acm)IDHLC(Acm).CF$_3$COOH, and then stirring carried out for 1 hour at room temperature. Cold ether was added to this solution, and the precipitate produced was centrifugally separated (3500 rpm, 5 min). After washing once again with cold ether and centrifuging, drying was carried out by means of a current of nitrogen. 64 ml of 50% DMSO-1N HCl was added to the solid obtained and stirring carried out overnight. Filtering was then carried out with a membrane filter (0.45 mm) and the filtrate purified by high performance liquid chromatography (column: YMC-Pack R&D ODS Size: 250×20 mm I.D. Particle: S-5 mm, 120A, 0.1% TFA-distilled water-0.1% TFA-acetonitrile gradient), after which, when the eluate was freeze dried, 18.6 mg (22.8 mmol) of C*IDHLC*.CF$_3$COOH was obtained (yield 73%).

Example 3

Synthesis of Cyclic Peptide by Means of an Amide Bond/Synthesis of D(CO—)ChgMet(O$_2$)dPhgLDpr(NH—) (SEQ ID NO:55) and D(CO—)ChgMet($O_2$)PhgLDpr(NH—) (SEQ ID NO:56)

500 mg of Fmoc-Dpr(Boc)-Pam resin (0.49 mmol/g) was treated twice with a 30% DMF solution of piperidine (15 ml, 5 mins), after which washing was carried out five times with 15 ml of DMF. A DMF solution (10 ml) of 173 mg of Fmoc-Leu-OH, 255 mg of PyBOP, 75 mg of HOBt and 80 ml of N-methylmorpholine was added and, after reacting for 1 hour, washing was carried out five times with 15 ml of DMF. By the same method, Fmoc-Phg-OH, Fmoc-Met($O_2$)—OH, Fmoc-Chg-OH and Fmoc-Asp(O-tBu)-OH were reacted in turn. 5 ml of a solution mixture of trifluoroacetic acid (94%), anisole (5%) and 1,2-ethanedithiol (1%) was added and reaction carried out for 2 hours, after which washing was performed with methanol (15 ml×5) and t-butyl methyl ether (15 ml×5), and then drying carried out under reduced pressure. After washing this with 15 ml of DMF, a DMF solution (10 ml) of 127 mg of PyBOP, 38 mg of HOBt and 40 ml of N-methylmorpholine was added, then reaction carried out for 1.5 hours and washing performed five times with DMF (15 ml). After treating twice with a 30% DMF solution of piperidine (15 ml, 5 mins), washing was carried out with methanol (15 ml×5) and t-butyl methyl ether (15 ml×5), and drying carried out under reduced pressure. After protective group removal with HF (1 hour), a mixture of ether/n-pentane (2:1) was added and the supernatant eliminated, following which 50% aqueous acetic acid solution was added to the residue and filtering performed. Next, the filtrate was freeze dried and after purifying by high performance liquid chromatography (column: YMC-Pack R&D ODS Size: 250×20 mmn I.D. Particle: S-5 mm, 120A, 0.1% TFA-distilled water-0.1% TFA-acetonitrile gradient), when freeze drying was carried out, there was obtained 9.5 mg of D(CO—)ChgMet($O_2$)PhgLDpr(NH—) (yield 10%) and 6.7 mg of D(CO—)ChgMet($O_2$)PhgLDpr(NH—) (yield 7%).

Using the same methods, the cyclic peptides shown in Table 1 were synthesised. In Table 1, there are shown the cyclization method, the cyclization yield and the physicochemical data for the cyclic peptides synthesized.

TABLE 1

Compound Cyclization Method, Yield and Analytical Data

| Sequence Number | Sequence | Cyclization Method | Yield | FAB MS | Amino Acid Analysis |
|---|---|---|---|---|---|
| 1 | C*IDSLC* | $K_3[Fe(CN)_6]$ | 62 | 651 | Asx 0.91, Ser 0.70, ½$Cys^2$ 2.59, Ile 0.88, Leu 0.92 |
| 2 | C*IDTLC* | $K_3[Fe(CN)_6]$ | 70 | 665 | Asx 0.97, Thr 0.89, ½$Cys^2$ 2.24, Ile 0.92, Leu 0.97 |
| 3 | C*IDYLC* | $K_3[Fe(CN)_6]$ | 61 | 727 | Asx 0.88, ½$Cys^2$ 2.51, Ile 0.85, Leu 0.89, Tyr 0.87 |
| 4 | C*IDHLC* | DMSO | 73 | 701 | Asx 0.88, ½$Cys^2$ 2.50, Ile 0.84, Leu 0.88, His 0.92 |
| 5 | C*dLDSLC* | DMSO | 77 | 651 | Asx 0.82, Ser 0.68, ½$Cys^2$ 2.86, Leu 1.64 |
| 6 | C*dLDdSLC* | DMSO | 62 | 651 | Asx 0.83, Ser 0.69, ½$Cys^2$ 2.81, Leu 1.67 |
| 7 | C*ADHLC* | DMSO | 59 | 659 | Asx 0.98, Ala 0.96, ½$Cys^2$ 1.93, Leu 0.98, His 0.98 |
| 8 | C*IDALC* | DMSO | 52 | 635 | Asx 1.09, Ala 1.07, ½$Cys^2$ 1.58, Ile 1.11, Leu 1.10 |
| 9 | C*IEHLC* | DMSO | 71 | 715 | Glx 0.96, ½$Cys^2$ 2.01, Ile 0.99, Leu 1.00, His 1.00 |
| 10 | C*INHLC* | DMSO | 85 | 700 | Asx 0.99, ½$Cys^2$ 1.99, Ile 1.00, Leu 1.00, His 1.00 |
| 11 | C*IDHLC*—$NH_2$ | DMSO | 58 | 700 | Asx 1.01, ½$Cys^2$ 1.89, Ile 1.02, Leu 1.02, His 1.06 |
| 12 | C*INHLC*—$NH_2$ | DMSO | 18 | 699 | Asx 1.03, ½$Cys^2$ 1.73, Ile 1.07, Leu 1.06, His 1.11 |
| 13 | AcC*IDHLC* | DMSO | 68 | 743 | Asx 0.97, ½$Cys^2$ 1.98, Ile 1.02, Leu 0.99, His 1.04 |
| 14 | Pen*IDHLC* | DMSO | 30 | 729 | Asx 1.14, ½$Cys^2$ 1.09, Ile 0.45, Leu 1.15, His 1.17 |
| 15 | dC*IDHLC* | DMSO | 39 | 701 | Asx 0.96, ½$Cys^2$ 2.11, Ile 0.96, Leu 0.98, His 0.98 |
| 16 | Mpr*IDHLC* | DMSO | 33 | 686 | Asx 0.99, ½$Cys^2$ 0.88, Ile 1.05, Leu 1.02, His 1.05 |
| 17 | C*IMet($O_2$)HLC* | DMSO | 68 | 749 | ½$Cys^2$ 1.66, Ile 1.02, Leu 1.10, His 1.09, Met($O_2$) 1.13 |
| 18 | C*IHseHLC* | DMSO | 56 | 687 | ½$Cys^2$ 1.71, Ile 0.99, Leu 1.02, His 1.06 |
| 19 | C*IYHLC* | DMSO | 52 | 749 | ½$Cys^2$ 2.13, Ile 0.93, Leu 0.99, Tyr 0.94, His 0.99 |
| 20 | C*IS(OMe)HLC* | DMSO | 52 | 749 | ½$Cys^2$ 2.13, Ile 0.93, Leu 0.99, Tyr 0.94, His 0.99 |
| 21 | C*dIDHLC* | DMSO | 72 | 701 | Asx 0.99, ½$Cys^2$ 1.91, Ile 1.04, Leu 1.02, His 1.04 |
| 22 | C*ChgDHLC* | DMSO | 68 | 727 | Asx 0.92, ½$Cys^2$ 1.95, Leu 0.92, His 0.93, Chg 1.28 |
| 23 | C*VDHLC* | DMSO | 75 | 687 | Asx 0.98, Val 0.99, ½$Cys^2$ 2.02, Leu 0.99, His 1.01 |
| 24 | C*TleDHLC* | DMSO | 69 | 701 | Asx 0.96, ½$Cys^2$ 1.99, Leu 0.99, His 0.99, Tle 1.07 |
| 25 | C*TicDHLC* | DMSO | 30 | 747 | Asx 0.98, ½$Cys^2$ 1.86, Leu 1.13, His 1.07, Tic 0.97 |
| 26 | C*PhgDHLC* | DMSO | 64 | 721 | Asx 0.95, ½$Cys^2$ 1.99, Leu 1.03, His 0.97, Phg 1.07 |
| 27 | C*dPhgDHLC* | DMSO | 55 | 721 | Asx 0.96, ½$Cys^2$ 1.95, Leu 1.02, His 0.97, Phg 1.05 |
| 28 | C*IDFLC* | DMSO | 50 | 711 | Asx 0.98, ½$Cys^2$ 2.09, Ile 0.97, Leu 0.98, Phe 0.98 |
| 29 | C*IDAla(2-Pyr)LC* | DMSO | 56 | 712 | Asx 1.16, ½$Cys^2$ 1.39, Ile 1.08, Leu 1.11, Ala(2-Pyr) 1.11 |
| 30 | C*IDdHLC* | DMSO | 74 | 701 | Asx 1.00, ½$Cys^2$ 1.93, Ile 1.01, Leu 1.01, His 1.03 |
| 31 | C*IDWLC* | DMSO | 47 | 750 | Asx 0.39, ½$Cys^2$ 2.67, Ile 1.26, Leu 1.33, Trp 0.34 |
| 32 | C*IDTleLC* | DMSO | 23 | 677 | Asx 0.99, ½$Cys^2$ 1.94, Ile 0.97, Leu 0.94, Tle 1.15 |
| 33 | C*IDHphLC* | DMSO | 38 | 725 | Asx 1.00, ½$Cys^2$ 1.94, Ile 0.98, Leu 1.00, Hph 1.05 |

*Total synthesis yield

TABLE 2

Compound Cyclization Method, Yield and Analytical Data

| Sequence Number | Sequence | Cyclization Method | Yield | FAB MS | Amino Acid Analysis |
|---|---|---|---|---|---|
| 34 | C*IDAla(2-Naph)LC* | DMSO | 38 | 761 | Asx 0.99, ½$Cys^2$ 2.03, Ile 0.98, Leu 1.00 |
| 35 | C*IDdPhgLC* | DMSO | 8 | 697 | Asx 0.99, ½$Cys^2$ 1.83, Ile 1.04, Leu 1.03, Phg 1.12 |

TABLE 2-continued

Compound Cyclization Method, Yield and Analytical Data

| Sequence Number | Sequence | Cyclization Method | Yield | FAB MS | Amino Acid Analysis |
|---|---|---|---|---|---|
| 36 | C*IDChaLC* | DMSO | 34 | 717 | Asx 0.98, ½Cys$^2$ 1.98, Ile 0.97, Leu 0.99, Cha 1.08 |
| 37 | C*IDPhgLC* | DMSO | 48 | 697 | Asx 0.99, ½Cys$^2$ 2.04, Ile 0.99, Leu <u>1.01</u>, Phg 0.96 |
| 38 | C*IDHdLC* | DMSO | 51 | 701 | Asx 0.96, ½Cys$^2$ 1.98, Ile 1.05, Leu 1.00, His 1.00 |
| 39 | C*ChgMet(O$_2$)HLC* | DMSO | 41 | 775 | ½Cys$^2$ 1.98, Leu 0.94, His 0.94, Met(O$_2$) 0.96, Chg 1.18 |
| 40 | C*ChgMet(O$_2$)dPhgLC* | DMSO | 8 | 771 | ½Cys$^2$ 1.88, Leu 0.99, Met(O$_2$) 0.97, Phg 1.03 Chg 1.13 |
| 41 | C*ChgMet(O$_2$)PhgLC* | DMSO | 4 | 771 | ½Cys$^2$ 1.72, Leu 1.05, Met(O$_2$) 1.01, Phg 1.08 Chg 1.14 |
| 42 | C*ChgMet(O$_2$)dHLC* | DMSO | 45 | 775 | ½Cys$^2$ 1.86, Leu 0.97, His 0.91, Met(O$_2$) 0.95, Chg 1.30 |
| 43 | C*ChgMet(O$_2$)dFLC* | DMSO | 26 | 785 | ½Cys$^2$ 1.92, Leu 0.97, Phe 0.95, Met(O$_2$) 0.98, Chg 1.18 |
| 44 | C*ChgMet(O$_2$)dYLC* | DMSO | 37 | 801 | ½Cys$^2$ 1.85, Leu 1.00, Tyr 0.95, Met(O$_2$) 0.96, Chg 1.13 |
| 45 | C*ChgMet(O$_2$)PhgIC* | DMSO | 3 | 771 | ½Cys$^2$ 1.81, Leu 0.97, Met(O$_2$) 1.01, Phg 1.01 Chg 1.17 |
| 46 | C*ChgMet(O$_2$)dPhgLdC* | DMSO | 40 | 771 | ½Cys$^2$ 1.62, Leu 1.01, Met(O$_2$) 0.97, Phg 1.05 Chg 1.22 |
| 47 | C*ChgMet(O$_2$)PhgLdC* | DMSO | 42 | 771 | ½Cys$^2$ 1.90, Leu 0.94, Met(O$_2$) 0.93, Phg 0.99 Chg 1.17 |
| 48 | C*IDFIC* | DMSO | 37 | 710 | Asx 0.92, ½Cys$^2$ 2.14, Ile 2.01, Phe 0.93 |
| 49 | C*ID(OMe)HLC* | DMSO | 34 | 715 | Asx 0.96, ½Cys$^2$ 1.99, Ile 1.02, Leu 0.99, His 1.04 |
| 50 | C*ID(OMe)HLC—OMe* | DMSO | 34 | 729 | Asx 1.02, ½Cys$^2$ 1.79, Ile 1.04, Leu 1.06, His 1.09 |
| 51 | C*IDHLC—OMe* | DMSO | 35 | 715 | Asx 1.02, ½Cys$^2$ 1.77, Ile 1.11, Leu 1.06, His 1.01 |
| 52 | C*IDHIC* | DMSO | 50 | 701 | Asx 1.07, ½Cys$^2$ 1.90, Ile 1.81, His 0.92 |
| 53 | C*IDHdPhgC* | DMSO | 37 | 721 | Asx 0.96, ½Cys$^2$ 1.71, Ile 0.90, His 1.04, dPhg 1.09 |
| 54 | C*IDHPhgC* | DMSO | 37 | 721 | Asx 0.92, ½Cys$^2$ 1.71, Ile 1.15, His 1.05, dPhg 1.17 |
| 55 | D(CO—)ChgMet(O$_2$)dPhgLDpr(NH—) | | 10* | 750 | Asx 0.95, Leu 0.96, Met(O$_2$) 0.85, Phg 0.95, Chg 1.11, Dap 1.07 |
| 56 | D(CO—)ChgMet(O$_2$)PhgLDap(NH—) | | 7* | 750 | Asx 0.95, Leu 0.96, Met(O$_2$) 0.85, Phg 0.99, Chg 1.11, Dap 1.09 |

*Total synthesis yield

Example 4

Cyclic peptide inhibiting effect in terms of the binding of CS-1 peptide and VLA-4-IgG chimeric protein.

A conjugate of the peptide containing the CS-1 sequence shown in SEQ ID NO:57 and rabbit IgG (Sigma) was prepared in accordance with the literature (Humphries, M. J. et al, J. Biol. Chem., 262, 6886–6892 (1987)). This was diluted with PBS(-), and 100 μl/well quantities introduced into a 96 well immunoplate (NUNC), after which this was left to stand for 16 hours at 4° C. and the CS-1 peptide immobilized.

Gys Lue His Gly Pro Glu Ile Leu Asp Val Pro Ser Thr (SEQ ID NO:57)

Next, after washing the interior of the wells twice with PBS(-), 300 μl/well quantities of 1% BSA-PBS solution which had been heat treated for 10 minutes at 80° C. were introduced, then left for 3 hours at 4° C., after which the solution inside the wells was removed by suction.

Each cyclic peptide and VLA-4-IgG chimeric protein (100 μl) were reacted together beforehand for 20 minutes at room temperature, and then reaction carried out for 3 hours at 30° C. with the CS-1 peptide. Subsequently, the non-bonded VLA-4-IgG chimeric protein was removed by suction, and washed away twice with TBS buffer (150 mM NaCl, 25 mM Tris-HCl, 1 mM MnCl$_2$, pH 7.4) containing 0.1% BSA. To the bonded VLA-4-IgG chimeric protein, biotin labelled anti-human IgG antibody (Vector) as the first antibody was added, and then avidin labelled horseradish peroxidase (Sigma) was added as the second antibody and reaction carried out. Following the reaction, o-phenylenediamine was added as a substrate and colour development effected, and then the absorbance measured at 490 nm. From this absorbance, the binding inhibition activity due to the respective peptides was determined. Of these, the inhibition activity of nine compounds is shown in Table 3.

TABLE 3

| Sequence Number | Sequence | Inhibition Activity (IC50: nM) |
|---|---|---|
| 4 | Cys* Ile Asp His Leu Cys* | 1200 |
| 9 | Cys* Ile Glu His Leu Cys* | 1600 |
| 17 | Cys* Ile Met(O$_2$) His Leu Cys* | 800 |
| 22 | Cys* Chg Asp His Leu Cys* | 120 |
| 25 | Cys* Tic Asp His Leu Cys* | 650 |
| 29 | Cys* Ile Asp Ala(2-Pyr) Leu Cys* | 500 |
| 31 | Cys* Ile Asp Trp Leu Cys* | 450 |
| 34 | Cys* Ile Asp Ala(2-Naph) Leu Cys* | 600 |
| 48 | Cys* Ile Asp Phe Ile Cys* | 250 |

Example 5
Effect of Cyclic Peptide in a Peritonitis Model

Ascaris crude extract (LSL Co.) was adjusted to 1 mg/ml with physiological saline solution and used as a sensitizing antigen. This antigen liquid was administered subcutaneously to BALB/c mice (female, 6 weeks old, Charles River Japan) at 100 μl on day-0 and day-1, taking the day of the commencement of sensitization as day-0, and 200 μl on day-8, to sensitize the mice. On day-13, 200 μl of the antigen liquid was administered intraperitoneally and peritonitis induced. 48 hours later, the mice were sacrificed by exsanguination, after which 3 ml of heparin-containing PBS was injected into the abdominal cavity, the abdomen opened and the abdominal lavage recovered. Following recovery, the white blood cells contained in the lavage were subjected to cytospin and a smear specimen prepared. After staining this specimen with May-Grunwald Giemsa stain, categorization of the white blood cells was carried out with a microscope and the number of eosinophils determined. The cyclic peptide shown in Sequence No.17, which was the test compound, was dissolved in PBS and 40 mg/kg was administered intraperitoneally 16 hours prior to the antigen challenge, at the time of the challenge, and 8 hours, 24 hours and 32 hours following the challenge. In the tests, there were 6–8 animals per group, and the results were expressed as an average±standard deviation. The test compound administration group and a control group were tested using the Student t-test and differences of level of significance p<0.05 were judged to be significant.

The results, as shown in FIG. 1, indicate that the cyclic peptide significantly (p<0.001) suppresses the accumulation of eosinophils in the abdomen due to antigen challenge. This result suggests that the cyclic peptide is effective in the treatment of allergy.

Example 6
Effect of Cyclic Peptide in an Ear Oedema Model 0.5% 2,4-dintrofluorobenzene (Aldrich; referred to below as DNFB) dissolved in acetone:olive oil (4:1) was applied to the backs of BALB/c type mice (female, 6 weeks old, Charles River Japan) and the mice sensitized. Taking the day of initial sensitization as day-0, sensitization was carried out twice, on day-0 and day-1. On day-5, 10 µl quantities of 0.2% DNFB solution dissolved in acetone:olive oil (4:1) were applied to both sides of the right ear of the mice, to induce ear oedema. The thickness of the right ear was measured prior to the challenge and 24 hours after the challenge using a Digimatic Indicator (Mitutoyo) and the percentage swelling of the ear calculated by means of the following formula.

swelling of the ear (%)=(A−B)/B×100

A: thickness of the right ear 24 hours after oedema induced
B: thickness of the right ear prior to oedema being induced The test compounds, namely dexamethasone (Sigma) or the cyclic peptide shown in SEQ ID NO:17, were dissolved in acetone and, just prior to the challenge, respectively 30 µg/ear or 1 mg/ear applied, and the effect investigated. In the tests, there were 6 animals per group and results were expressed as the average±standard deviation. The compound administration groups and a control group were tested using the Student t-test and differences of level of significance p<0.05 were judged to be significant.

Figure 2:
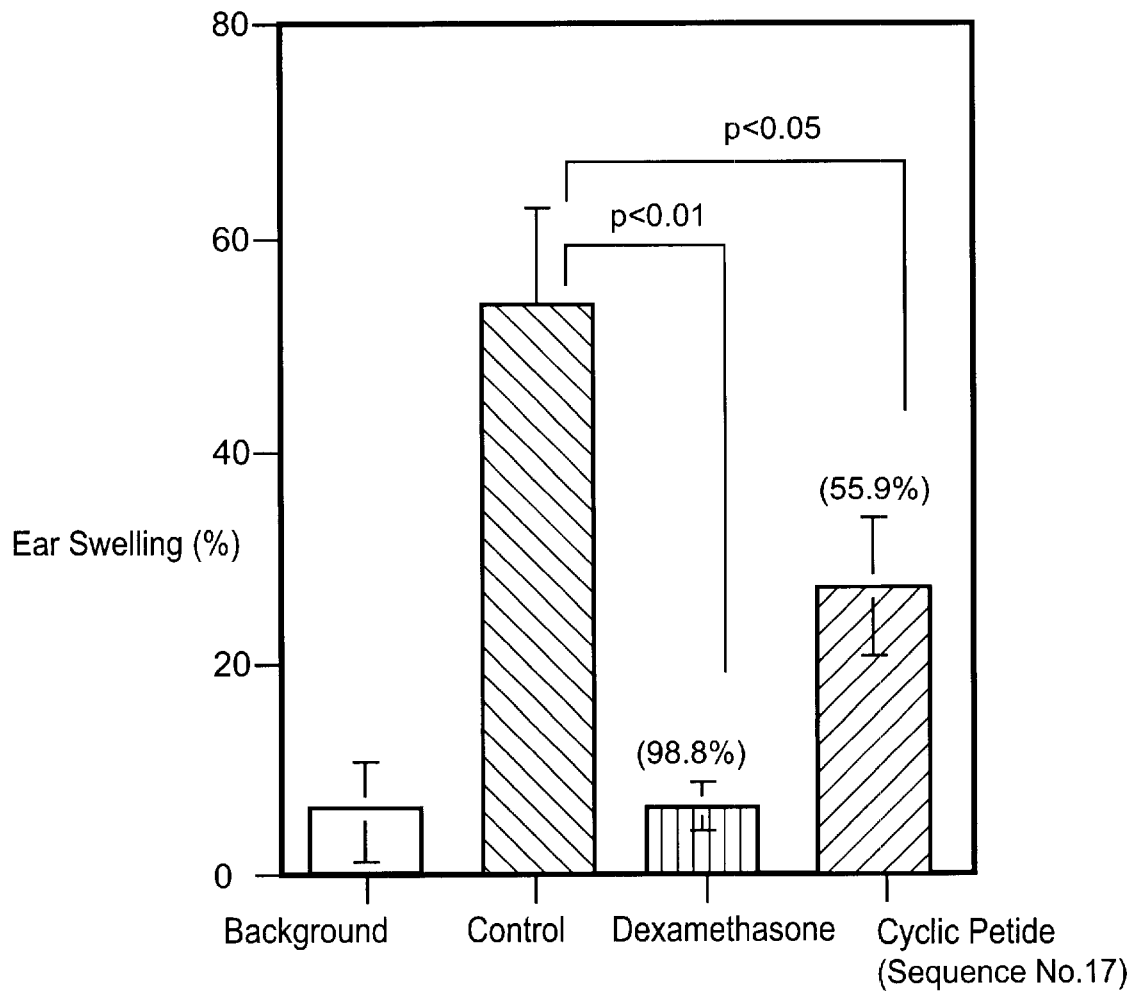
FIG. 2 shows the fact that, in the mouse ear oedema model, cyclic peptide shown in SEQ ID NO:17 significantly suppressed ear swelling induced by dinitrofluorobenzene application.

The results, as shown in FIG. 2, indicate that the dexamethasone or the cyclic peptide (Sequence No.17) clearly significantly suppress ear oedema induced by antigen application (respectively p<0.001, p<0.05). This result suggests that it is effective in the treatment of allergic inflammation, in particular contact hypersensitivity and other forms of allergic disease.

Example 7
Effect of Cyclic Peptide Against Liver Injury

Hepatitis was induced in 9 week old male BALB/c mice by the intravenous administration of 20 mg/kg of concanavalin A (ConA). 8 hours after the ConA administration, the peripheral blood was sampled and, following centrifugation, the serum was removed. The aspartate aminotransferase (AST) and alanine aminotransferase (ALT) in the serum, which are liver function markets, were measured using a biochemical analyser (Ciba Corning 55), and used as an index of the severity of the hepatitis. The cyclic peptide of Sequence No. 17, which was the test agent, was intravenously/intra-abdominally administered at a dose of 100 or 500 µg/kg, 16 hours prior to the ConA challenge and just prior to the challenge. The tests were carried out with 6 animals per group and the results were expressed as the average±standard deviation.

The results, as shown in Table 4, show clearly that the cyclic peptide of Sequence No.17 suppresses the rise in AST and ALT due to ConA administration. This result indicates that the cyclic peptide is effective in the treatment of liver injury.

| Cyclic Peptide Administered | Suppression of Increase in AST (%) | Suppression of Increase in ALT (%) |
|---|---|---|
| Sequence No.17 100 µg/kg | 27.0 | 38.7 |
| Sequence No.17 500 µg/kg | 48.0 | 49.5 |

Industrial Applicability

By means of the present invention, there have been created novel cyclic peptides or salts thereof which have a VLA-4 adhesion molecule inhibiting action, and it has been discovered that they are useful as therapeutic agents for inflammatory diseases, for example allergic inflammatory disease, hepatitis, autoimmune diseases, rejection reactions following organ transplantation, type I diabetes, Crohn's disease, or postoperative restenosis prevention and arteriosclerosis.

What is claimed is:

1. A cyclic peptide represented by formula (I)

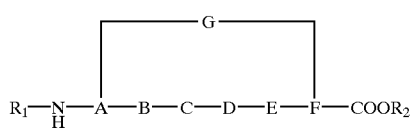

where, in formula (I),

A and F may be the same or different, and are both selected from the group consisting of L- or D-form Cys, homo-Cys, Pen and Mpr, B is selected from the group consisting of L- or D-form Ala, Ala(t-Bu), Val, Leu, Ile, aIle, Abu, Nle, Nva, Tle, Cha, Chg, Phe, Phg, Trp, Ala(3-Bzt), Ala(1-Naph), Ala(2-Naph), Ala(2-Pyr), Ala(2-Qui), His, Thi, Ala(4-Thz), 2-Abz, Pro, homo-Pro and Tic, C is selected from the group consisting of L-form Asp analogues, Glu analogues, Aad analogues, Asn analogues, Gln analogues, Ser, Ser(OMe), homo-Ser, Dpr, Dab, Orn, Met, Met(O), Met($O_2$), aIle, Nle, Nva, Chg, Phg, Tyr and Tle and, when C is selected from the group consisting of the L-form Asp analogues, Glu analogues and Aad analogues, then C is of formula (II)

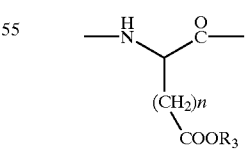

n=1 Asp n=2 Glu n=3 Aad
where $R_3$ may be hydrogen or a $C_1$ to $C_6$ straight chain or branched alkyl group, provided that when C is an Asn analogue or a Gln analogue, then C is of formula (III)

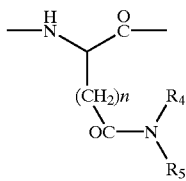

n=1 Asn  n=2 Gln where $R_4$ and $R_5$ may be the same or different, and may respectively be hydrogen or a $C_1$ to $C_6$ straight chain or branched alkyl group, D is selected from the group consisting of L- or D-form Tyr, Ser, homo-Ser, Leu, Ile, aIle, Nle, Nva, Chg, Cha, Val, Ala(t-Bu), Abu, Tle, Ala, Phg, homo-Phe, Phe, Ala(2-Naph), Ala(2-Pyr), Ala(3-Bzt), Ala(1-Naph), Ala(2-Qui), Thi, Ala(4-Thz), 2-Abz, Trp and His, E is selected from the group consisting of L- or D-form Leu, Ile, aIle, Nle, Nva, Chg, Cha, Tle, Phg, homo-Phe, Ala(2-Naph), Ala(2-Pyr), Ala(3-Bzt), Ala(1-Naph), Ala(2-Qui), Thi, Ala(4-Thz), 2-Abz and His, G represents a disulphide bond, $R_1$ may be hydrogen or an acyl group, and in the case where $R_1$ is an acyl group, then $R_1$ is of formula (IV)

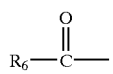

where $R_6$ is selected from the group consisting of a $C_1$ to $C_6$ straight chain or branched alkyl group, a $C_4$ to $C_8$ cycloalkyl group, a $C_5$ to $C_{11}$ alkylcycloalkyl group, a $C_6$ to $C_{14}$ aryl group or a $C_7$ to $C_{11}$ aralkyl group, and $R_2$ may be hydrogen or a $C_1$ to $C_6$ straight chain alkyl or branched alkyl group, or salts thereof.

2. A cyclic peptide or salt thereof according to claim 1 wherein C is selected from the group consisting of L-form Ser, Ser(OMe), homo-Ser, Dpr, Dab, Orn, Met(O), Met($O_2$), aIle, Nle, Nva, Chg, Phg, Tyr and Tle, and D is selected from the group consisting of L- or D-form Tyr, Ser, homo-Ser, Leu, Ile, aIle, Nle, Nva, Chg, Val, Ala(t-Bu), Abu, Tle, Ala, Phg, homo-Phe, Ala(2-Naph), Ala(2-Pyr), Ala(3-Bzt), Ala(1-Naph), Ala(2-Qui), Thi, Ala(4-Thz), 2-Abz, Trp and His.

3. A cyclic peptide or salt thereof according to claim 1 where B is selected from the group consisting of L- or D-form Ala, Ala(t-Bu), Val, Leu, Ile, aIle, Abu, Nle, Nva, Tle, Cha, Chg, Phe, Phg, Trp, His, Pro, homo-Pro and Tic, C is selected from the group consists of L-form Ser, Ser(OMe), homo-Ser, Met(O), Met($O_2$), aIle, Nle, Nva, Chg, Phg, Tyr and Tle, D is selected from the group consists of L- or D-form Tyr, Ser, homo-Ser, Leu, Ile, aIle, Nle, Nva, Chg, Val, Ala(t-Bu), Abu, Tle, Ala, Phg, homo-Phe, Ala(2-Naph), Ala(2-Pyr), Ala(1-Naph), Ala(2-Qui), Trp and His, E is selected from the group consists of L- or D-form Leu, Ile, aIle, Nle, Nva, Chg, Cha, Tle, Phg, homo-Phe and His, G is a disulphide bond, $R_1$ may be hydrogen or an acyl group and, in the case where $R_1$ is an acyl group, it is represented by formula (IV), where $R_6$ in formula (IV) comprises a $C_1$ to $C_6$ straight chain alkyl group, and $R_2$ may be hydrogen or a $C_1$ to $C_6$ straight chain alkyl group.

4. A cyclic peptide or salt thereof according to claim 1 where $R_1$ is hydrogen or is represented by formula (IV) and, in the case where $R_1$ is represented by formula (IV), $R_6$ comprises a $C_1$ to $C_6$ straight chain alkyl group, and $R_2$ may be hydrogen or a $C_1$ to $C_6$ straight chain alkyl group.

5. A therapeutic composition comprising a cyclic peptide of claim 1 together with a pharmaceutically acceptable carrier or diluent.

6. A method of treating allergic inflammatory disease or hepatitis comprising administering to a subject an effective amount of a cyclic peptide of claim 1 having VLA-4 adhesion activity.

* * * * *

SEQUENCE LISTING

<160> NUMBER OF SEQ ID NOS: 57

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Cyclic peptide
<221> NAME/KEY: DISULFID
<222> LOCATION: (1)..(6)
<223> OTHER INFORMATION: Disulfide-bond

<400> SEQUENCE: 1

Cys Ile Asp Ser Leu Cys
 1               5

```
<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide
<221> NAME/KEY: DISULFID
<222> LOCATION: (1)..(6)
<223> OTHER INFORMATION: Disulfide-bond

<400> SEQUENCE: 2

Cys Ile Asp Thr Leu Cys
  1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide
<221> NAME/KEY: DISULFID
<222> LOCATION: (1)..(6)
<223> OTHER INFORMATION: Disulfide-bond

<400> SEQUENCE: 3

Cys Ile Asp Tyr Leu Cys
  1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide
<221> NAME/KEY: DISULFID
<222> LOCATION: (1)..(6)
<223> OTHER INFORMATION: Disulfide-bond

<400> SEQUENCE: 4

Cys Ile Asp His Leu Cys
  1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide
<221> NAME/KEY: DISULFID
<222> LOCATION: (1)..(6)
<223> OTHER INFORMATION: Disulfide-bond
<221> NAME/KEY: MOD_RES
<222> LOCATION: (2)
<223> OTHER INFORMATION: d-Leu

<400> SEQUENCE: 5

Cys Xaa Asp Ser Leu Cys
  1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide
<221> NAME/KEY: DISULFID
```

```
<222> LOCATION: (1)..(6)
<223> OTHER INFORMATION: Disulfide-bond
<221> NAME/KEY: MOD_RES
<222> LOCATION: (2)
<223> OTHER INFORMATION: d-Leu
<221> NAME/KEY: MOD_RES
<222> LOCATION: (4)
<223> OTHER INFORMATION: d-Ser

<400> SEQUENCE: 6

Cys Xaa Asp Xaa Leu Cys
 1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide
<221> NAME/KEY: DISULFID
<222> LOCATION: (1)..(6)
<223> OTHER INFORMATION: Disulfide-bond

<400> SEQUENCE: 7

Cys Ala Asp His Leu Cys
 1               5

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide
<221> NAME/KEY: DISULFID
<222> LOCATION: (1)..(6)
<223> OTHER INFORMATION: Disulfide-bond

<400> SEQUENCE: 8

Cys Ile Asp Ala Leu Cys
 1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide
<221> NAME/KEY: DISULFID
<222> LOCATION: (1)..(6)
<223> OTHER INFORMATION: Disulfide-bond

<400> SEQUENCE: 9

Cys Ile Glu His Leu Cys
 1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide
<221> NAME/KEY: DISULFID
<222> LOCATION: (1)..(6)
<223> OTHER INFORMATION: Disulfide-bond

<400> SEQUENCE: 10
```

```
Cys Ile Asn His Leu Cys
  1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide
<221> NAME/KEY: DISULFID
<222> LOCATION: (1)..(6)
<223> OTHER INFORMATION: Disulfide-bond
<221> NAME/KEY: MOD_RES
<222> LOCATION: (6)
<223> OTHER INFORMATION: Cys-carboxamide

<400> SEQUENCE: 11

Cys Ile Asp His Leu Xaa
  1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide
<221> NAME/KEY: DISULFID
<222> LOCATION: (1)..(6)
<223> OTHER INFORMATION: Disulfide-bond
<221> NAME/KEY: MOD_RES
<222> LOCATION: (6)
<223> OTHER INFORMATION: Cys-carboxamide

<400> SEQUENCE: 12

Cys Ile Asn His Leu Xaa
  1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide
<221> NAME/KEY: DISULFID
<222> LOCATION: (1)..(6)
<223> OTHER INFORMATION: Disulfide-bond
<221> NAME/KEY: MOD_RES
<222> LOCATION: (1)
<223> OTHER INFORMATION: N-acetyl-Cys

<400> SEQUENCE: 13

Xaa Ile Asp His Leu Cys
  1               5

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide
<221> NAME/KEY: DISULFID
<222> LOCATION: (1)..(6)
<223> OTHER INFORMATION: Disulfide-bond
<221> NAME/KEY: MOD_RES
<222> LOCATION: (1)
<223> OTHER INFORMATION: penicillamine

<400> SEQUENCE: 14
```

```
Xaa Ile Asp His Leu Cys
 1               5
```

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide
<221> NAME/KEY: DISULFID
<222> LOCATION: (1)..(6)
<223> OTHER INFORMATION: Disulfide-bond
<221> NAME/KEY: MOD_RES
<222> LOCATION: (1)
<223> OTHER INFORMATION: d-Cys

<400> SEQUENCE: 15

```
Xaa Ile Asp His Leu Cys
 1               5
```

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide
<221> NAME/KEY: DISULFID
<222> LOCATION: (1)..(6)
<223> OTHER INFORMATION: Disulfide-bond
<221> NAME/KEY: MOD_RES
<222> LOCATION: (1)
<223> OTHER INFORMATION: 3-mercaptopropionic acid

<400> SEQUENCE: 16

```
Xaa Ile Asp His Leu Cys
 1               5
```

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide
<221> NAME/KEY: DISULFID
<222> LOCATION: (1)..(6)
<223> OTHER INFORMATION: Disulfide-bond
<221> NAME/KEY: MOD_RES
<222> LOCATION: (3)
<223> OTHER INFORMATION: methionine sulfone

<400> SEQUENCE: 17

```
Cys Ile Xaa His Leu Cys
 1               5
```

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide
<221> NAME/KEY: DISULFID
<222> LOCATION: (1)..(6)
<223> OTHER INFORMATION: Disulfide-bond
<221> NAME/KEY: MOD_RES
<222> LOCATION: (3)
<223> OTHER INFORMATION: homo-serine

```
<400> SEQUENCE: 18

Cys Ile Xaa His Leu Cys
  1               5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide
<221> NAME/KEY: DISULFID
<222> LOCATION: (1)..(6)
<223> OTHER INFORMATION: Disulfide-bond

<400> SEQUENCE: 19

Cys Ile Tyr His Leu Cys
  1               5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide
<221> NAME/KEY: DISULFID
<222> LOCATION: (1)..(6)
<223> OTHER INFORMATION: Disulfide-bond
<221> NAME/KEY: MOD_RES
<222> LOCATION: (3)
<223> OTHER INFORMATION: O-methyl-serine

<400> SEQUENCE: 20

Cys Ile Xaa His Leu Cys
  1               5

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide
<221> NAME/KEY: DISULFID
<222> LOCATION: (1)..(6)
<223> OTHER INFORMATION: Disulfide-bond
<221> NAME/KEY: MOD_RES
<222> LOCATION: (2)
<223> OTHER INFORMATION: d-Ile

<400> SEQUENCE: 21

Cys Xaa Asp His Leu Cys
  1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide
<221> NAME/KEY: DISULFID
<222> LOCATION: (1)..(6)
<223> OTHER INFORMATION: Disulfide-bond
<221> NAME/KEY: MOD_RES
<222> LOCATION: (2)
<223> OTHER INFORMATION: cyclohexylglycine

<400> SEQUENCE: 22
```

```
Cys Xaa Asp His Leu Cys
 1               5
```

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide
<221> NAME/KEY: DISULFID
<222> LOCATION: (1)..(6)
<223> OTHER INFORMATION: Disulfide-bond

<400> SEQUENCE: 23

```
Cys Val Asp His Leu Cys
 1               5
```

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide
<221> NAME/KEY: DISULFID
<222> LOCATION: (1)..(6)
<223> OTHER INFORMATION: Disulfide-bond
<221> NAME/KEY: MOD_RES
<222> LOCATION: (2)
<223> OTHER INFORMATION: tert-butylglycine

<400> SEQUENCE: 24

```
Cys Xaa Asp His Leu Cys
 1               5
```

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide
<221> NAME/KEY: DISULFID
<222> LOCATION: (1)..(6)
<223> OTHER INFORMATION: Disulfide-bond
<221> NAME/KEY: MOD_RES
<222> LOCATION: (2)
<223> OTHER INFORMATION: 1, 2, 3, 4-tetrahydroisoquinoline-3-carboxylic
      acid

<400> SEQUENCE: 25

```
Cys Xaa Asp His Leu Cys
 1               5
```

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide
<221> NAME/KEY: DISULFID
<222> LOCATION: (1)..(6)
<223> OTHER INFORMATION: Disulfide-bond
<221> NAME/KEY: MOD_RES
<222> LOCATION: (2)
<223> OTHER INFORMATION: phenylglycine

<400> SEQUENCE: 26

```
Cys Xaa Asp His Leu Cys
```

```
<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide
<221> NAME/KEY: DISULFID
<222> LOCATION: (1)..(6)
<223> OTHER INFORMATION: Disulfide-bond
<221> NAME/KEY: MOD_RES
<222> LOCATION: (2)
<223> OTHER INFORMATION: d-phenylglycine

<400> SEQUENCE: 27

Cys Xaa Asp His Leu Cys
 1               5

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide
<221> NAME/KEY: DISULFID
<222> LOCATION: (1)..(6)
<223> OTHER INFORMATION: Disulfide-bond

<400> SEQUENCE: 28

Cys Ile Asp Phe Leu Cys
 1               5

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide
<221> NAME/KEY: DISULFID
<222> LOCATION: (1)..(6)
<223> OTHER INFORMATION: Disulfide-bond
<221> NAME/KEY: MOD_RES
<222> LOCATION: (4)
<223> OTHER INFORMATION: 2-pyridylalanine

<400> SEQUENCE: 29

Cys Ile Asp Xaa Leu Cys
 1               5

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide
<221> NAME/KEY: DISULFID
<222> LOCATION: (1)..(6)
<223> OTHER INFORMATION: Disulfide-bond
<221> NAME/KEY: MOD_RES
<222> LOCATION: (4)
<223> OTHER INFORMATION: d-His

<400> SEQUENCE: 30

Cys Ile Asp Xaa Leu Cys
 1               5
```

```
<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide
<221> NAME/KEY: DISULFID
<222> LOCATION: (1)..(6)
<223> OTHER INFORMATION: Disulfide-bond

<400> SEQUENCE: 31

Cys Ile Asp Trp Leu Cys
  1               5

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide
<221> NAME/KEY: DISULFID
<222> LOCATION: (1)..(6)
<223> OTHER INFORMATION: Disulfide-bond
<221> NAME/KEY: MOD_RES
<222> LOCATION: (4)
<223> OTHER INFORMATION: tert-butylglycine

<400> SEQUENCE: 32

Cys Ile Asp Xaa Leu Cys
  1               5

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide
<221> NAME/KEY: DISULFID
<222> LOCATION: (1)..(6)
<223> OTHER INFORMATION: Disulfide-bond
<221> NAME/KEY: MOD_RES
<222> LOCATION: (4)
<223> OTHER INFORMATION: homo-phenylalanine

<400> SEQUENCE: 33

Cys Ile Asp Xaa Leu Cys
  1               5

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide
<221> NAME/KEY: DISULFID
<222> LOCATION: (1)..(6)
<223> OTHER INFORMATION: Disulfide-bond
<221> NAME/KEY: MOD_RES
<222> LOCATION: (4)
<223> OTHER INFORMATION: 2-naphtylalanine

<400> SEQUENCE: 34

Cys Ile Asp Xaa Leu Cys
  1               5

<210> SEQ ID NO 35
```

```
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide
<221> NAME/KEY: DISULFID
<222> LOCATION: (1)..(6)
<223> OTHER INFORMATION: Disulfide-bond
<221> NAME/KEY: MOD_RES
<222> LOCATION: (4)
<223> OTHER INFORMATION: d-phenylglycine

<400> SEQUENCE: 35

Cys Ile Asp Xaa Leu Cys
  1               5

<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide
<221> NAME/KEY: DISULFID
<222> LOCATION: (1)..(6)
<223> OTHER INFORMATION: Disulfide-bond
<221> NAME/KEY: MOD_RES
<222> LOCATION: (4)
<223> OTHER INFORMATION: cyclohexylalanine

<400> SEQUENCE: 36

Cys Ile Asp Xaa Leu Cys
  1               5

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide
<221> NAME/KEY: DISULFID
<222> LOCATION: (1)..(6)
<223> OTHER INFORMATION: Disulfide-bond
<221> NAME/KEY: MOD_RES
<222> LOCATION: (4)
<223> OTHER INFORMATION: phenylglycine

<400> SEQUENCE: 37

Cys Ile Asp Xaa Leu Cys
  1               5

<210> SEQ ID NO 38
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide
<221> NAME/KEY: DISULFID
<222> LOCATION: (1)..(6)
<223> OTHER INFORMATION: Disulfide-bond
<221> NAME/KEY: MOD_RES
<222> LOCATION: (5)
<223> OTHER INFORMATION: d-Leu

<400> SEQUENCE: 38

Cys Ile Asp His Xaa Cys
  1               5
```

```
<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide
<221> NAME/KEY: DISULFID
<222> LOCATION: (1)..(6)
<223> OTHER INFORMATION: Disulfide-bond
<221> NAME/KEY: MOD_RES
<222> LOCATION: (2)
<223> OTHER INFORMATION: cyclohexylglycine
<221> NAME/KEY: MOD_RES
<222> LOCATION: (3)
<223> OTHER INFORMATION: methionine sulfone

<400> SEQUENCE: 39

Cys Xaa Xaa His Leu Cys
 1               5

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide
<221> NAME/KEY: DISULFID
<222> LOCATION: (1)..(6)
<223> OTHER INFORMATION: Disulfide-bond
<221> NAME/KEY: MOD_RES
<222> LOCATION: (2)
<223> OTHER INFORMATION: cyclohexylglycine
<221> NAME/KEY: MOD_RES
<222> LOCATION: (3)
<223> OTHER INFORMATION: methionine sulfone
<221> NAME/KEY: MOD_RES
<222> LOCATION: (4)
<223> OTHER INFORMATION: d-phenylglycine

<400> SEQUENCE: 40

Cys Xaa Xaa Xaa Leu Cys
 1               5

<210> SEQ ID NO 41
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide
<221> NAME/KEY: DISULFID
<222> LOCATION: (1)..(6)
<223> OTHER INFORMATION: Disulfide-bond
<221> NAME/KEY: MOD_RES
<222> LOCATION: (2)
<223> OTHER INFORMATION: cyclohexylglycine
<221> NAME/KEY: MOD_RES
<222> LOCATION: (3)
<223> OTHER INFORMATION: methionine sulfone
<221> NAME/KEY: MOD_RES
<222> LOCATION: (4)
<223> OTHER INFORMATION: Phg

<400> SEQUENCE: 41

Cys Xaa Xaa Xaa Leu Cys
 1               5

<210> SEQ ID NO 42
<211> LENGTH: 6
<212> TYPE: PRT
<213> ORGANISM: Artificial Sequence
```

```
<220> FEATURE:
<223> OTHER INFORMATION: Description of Artificial Sequence: Cyclic
      peptide
<221> NAME/KEY: DISULFID
<222> LOCATION: (1)..(6)
<223> OTHER INFORMATION: Disulfide-bond
<221> NAME/KEY: MOD_RES
<222> LOCATION: (2)
<223> OTHER INFORMATION: cyclohexylglycine
<221> NAME/KEY: MOD_RES
<222> LOCATION: (3)
<223> OTHER INFORMATION: methionine sulfone
<221> NAME/KEY: MOD_RES
<222> LOCATION: (4)
<223> OTHER INFORMATION: d-His

<400> SEQUENCE: 42

Cys Xaa Xaa Xaa Leu Cys
 1               5

<210> SEQ ID NO 43
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide
<221> NAME/KEY: DISULFID
<222> LOCATION: (1)..(6)
<223> OTHER INFORMATION: Disulfide-bond
<221> NAME/KEY: MOD_RES
<222> LOCATION: (2)
<223> OTHER INFORMATION: cyclohexylglycine
<221> NAME/KEY: MOD_RES
<222> LOCATION: (3)
<223> OTHER INFORMATION: methionine sulfone
<221> NAME/KEY: MOD_RES
<222> LOCATION: (4)
<223> OTHER INFORMATION: d-Phe

<400> SEQUENCE: 43

Cys Xaa Xaa Xaa Leu Cys
 1               5

<210> SEQ ID NO 44
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide
<221> NAME/KEY: DISULFID
<222> LOCATION: (1)..(6)
<223> OTHER INFORMATION: Disulfide-bond
<221> NAME/KEY: MOD_RES
<222> LOCATION: (2)
<223> OTHER INFORMATION: cyclohexylglycine
<221> NAME/KEY: MOD_RES
<222> LOCATION: (3)
<223> OTHER INFORMATION: methionine sulfone
<221> NAME/KEY: MOD_RES
<222> LOCATION: (4)
<223> OTHER INFORMATION: d-Tyr

<400> SEQUENCE: 44

Cys Xaa Xaa Xaa Leu Cys
 1               5

<210> SEQ ID NO 45
<211> LENGTH: 6
<212> TYPE: PRT
<213> ORGANISM: Artificial Sequence
<220> FEATURE:
```

```
<223> OTHER INFORMATION: Description of Artificial Sequence: Cyclic
      peptide
<221> NAME/KEY: DISULFID
<222> LOCATION: (1)..(6)
<223> OTHER INFORMATION: Disulfide-bond
<221> NAME/KEY: MOD_RES
<222> LOCATION: (2)
<223> OTHER INFORMATION: cyclohexylglycine
<221> NAME/KEY: MOD_RES
<222> LOCATION: (3)
<223> OTHER INFORMATION: methionine sulfone
<221> NAME/KEY: MOD_RES
<222> LOCATION: (4)
<223> OTHER INFORMATION: phenylglycine

<400> SEQUENCE: 45

Cys Xaa Xaa Xaa Ile Cys
 1               5

<210> SEQ ID NO 46
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide
<221> NAME/KEY: DISULFID
<222> LOCATION: (1)..(6)
<223> OTHER INFORMATION: Disulfide-bond
<221> NAME/KEY: MOD_RES
<222> LOCATION: (2)
<223> OTHER INFORMATION: cyclohexylglycine
<221> NAME/KEY: MOD_RES
<222> LOCATION: (3)
<223> OTHER INFORMATION: methionine sulfone
<221> NAME/KEY: MOD_RES
<222> LOCATION: (4)
<223> OTHER INFORMATION: d-phenylglycine
<221> NAME/KEY: MOD_RES
<222> LOCATION: (6)
<223> OTHER INFORMATION: d-Cys

<400> SEQUENCE: 46

Cys Xaa Xaa Xaa Leu Xaa
 1               5

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide
<221> NAME/KEY: DISULFID
<222> LOCATION: (1)..(6)
<223> OTHER INFORMATION: Disulfide-bond
<221> NAME/KEY: MOD_RES
<222> LOCATION: (2)
<223> OTHER INFORMATION: cyclohexylglycine
<221> NAME/KEY: MOD_RES
<222> LOCATION: (3)
<223> OTHER INFORMATION: methionine sulfone
<221> NAME/KEY: MOD_RES
<222> LOCATION: (4)
<223> OTHER INFORMATION: phenylglycine
<221> NAME/KEY: MOD_RES
<222> LOCATION: (6)
<223> OTHER INFORMATION: d-Cys

<400> SEQUENCE: 47

Cys Xaa Xaa Xaa Leu Xaa
 1               5
```

```
<210> SEQ ID NO 48
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide
<221> NAME/KEY: DISULFID
<222> LOCATION: (1)..(6)
<223> OTHER INFORMATION: Disulfide-bond

<400> SEQUENCE: 48

Cys Ile Asp Phe Ile Cys
  1               5

<210> SEQ ID NO 49
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide
<221> NAME/KEY: DISULFID
<222> LOCATION: (1)..(6)
<223> OTHER INFORMATION: Disulfide-bond
<221> NAME/KEY: MOD_RES
<222> LOCATION: (3)
<223> OTHER INFORMATION: Asp B-methyl ester

<400> SEQUENCE: 49

Cys Ile Xaa His Leu Cys
  1               5

<210> SEQ ID NO 50
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide
<221> NAME/KEY: DISULFID
<222> LOCATION: (1)..(6)
<223> OTHER INFORMATION: Disulfide-bond
<221> NAME/KEY: MOD_RES
<222> LOCATION: (3)
<223> OTHER INFORMATION: Asp B-methyl ester
<221> NAME/KEY: MOD_RES
<222> LOCATION: (6)
<223> OTHER INFORMATION: Cys methyl ester

<400> SEQUENCE: 50

Cys Ile Xaa His Leu Xaa
  1               5

<210> SEQ ID NO 51
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide
<221> NAME/KEY: DISULFID
<222> LOCATION: (1)..(6)
<223> OTHER INFORMATION: Disulfide-bond
<221> NAME/KEY: MOD_RES
<222> LOCATION: (6)
<223> OTHER INFORMATION: Cys methyl ester

<400> SEQUENCE: 51

Cys Ile Asp His Leu Xaa
  1               5
```

<210> SEQ ID NO 52
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide
<221> NAME/KEY: DISULFID
<222> LOCATION: (1)..(6)
<223> OTHER INFORMATION: Disulfide-bond

<400> SEQUENCE: 52

Cys Ile Asp His Ile Cys
 1               5

<210> SEQ ID NO 53
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide
<221> NAME/KEY: DISULFID
<222> LOCATION: (1)..(6)
<223> OTHER INFORMATION: Disulfide-bond
<221> NAME/KEY: MOD_RES
<222> LOCATION: (5)
<223> OTHER INFORMATION: d-phenylglycine

<400> SEQUENCE: 53

Cys Ile Asp His Xaa Cys
 1               5

<210> SEQ ID NO 54
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide
<221> NAME/KEY: DISULFID
<222> LOCATION: (1)..(6)
<223> OTHER INFORMATION: Disulfide-bond
<221> NAME/KEY: MOD_RES
<222> LOCATION: (5)
<223> OTHER INFORMATION: phenylglycine

<400> SEQUENCE: 54

Cys Ile Asp His Xaa Cys
 1               5

<210> SEQ ID NO 55
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide
<221> NAME/KEY: DISULFID
<222> LOCATION: (1)..(6)
<223> OTHER INFORMATION: Disulfide-bond
<221> NAME/KEY: MOD_RES
<222> LOCATION: (2)
<223> OTHER INFORMATION: cyclohexylglycine
<221> NAME/KEY: MOD_RES
<222> LOCATION: (3)
<223> OTHER INFORMATION: methionine sulfone
<221> NAME/KEY: MOD_RES
<222> LOCATION: (4)
<223> OTHER INFORMATION: d-phenylglycine
<221> NAME/KEY: MOD_RES
<222> LOCATION: (6)

```
<223> OTHER INFORMATION: 2, 3-diaminopropionic acid

<400> SEQUENCE: 55

Asp Xaa Xaa Xaa Leu Xaa
 1               5

<210> SEQ ID NO 56
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide
<221> NAME/KEY: DISULFID
<222> LOCATION: (1)..(6)
<223> OTHER INFORMATION: Disulfide-bond
<221> NAME/KEY: MOD_RES
<222> LOCATION: (2)
<223> OTHER INFORMATION: cyclohexylglycine
<221> NAME/KEY: MOD_RES
<222> LOCATION: (3)
<223> OTHER INFORMATION: methionine sulfone
<221> NAME/KEY: MOD_RES
<222> LOCATION: (4)
<223> OTHER INFORMATION: phenylglycine
<221> NAME/KEY: MOD_RES
<222> LOCATION: (6)
<223> OTHER INFORMATION: 2, 3-diaminopropionic acid

<400> SEQUENCE: 56

Asp Xaa Xaa Xaa Leu Xaa
 1               5

<210> SEQ ID NO 57
<211> LENGTH: 13
<212> TYPE: PRT
<213> ORGANISM: Artificial Sequence
<220> FEATURE:
<223> OTHER INFORMATION: Description of Artificial Sequence: Cyclic
      peptide

<400> SEQUENCE: 57

Cys Leu His Gly Pro Glu Ile Leu Asp Val Pro Ser Thr
 1               5                  10
```